United States Patent [19]

Marsili et al.

[11] 4,017,481

[45] Apr. 12, 1977

[54] RIFAMYCIN COMPOUNDS

[75] Inventors: Leonardo Marsili, Segrate, (Milan); Vittorio Rossetti, Melzo, (Milan); Carmine Pasqualucci, Milan, all of Italy

[73] Assignee: Archifar Industrie Chimiche del Trentino S.p.A., Rovereto, Italy

[22] Filed: Apr. 27, 1976

[21] Appl. No.: 680,771

[30] Foreign Application Priority Data

May 15, 1975 Italy .................. 5155/75

[52] U.S. Cl. .................. 260/239.3 P; 424/244
[51] Int. Cl.² .................. C07D 498/08
[58] Field of Search .................. 260/239.3 P

[56] References Cited

FOREIGN PATENTS OR APPLICATIONS 1,670,377  2/1974  Germany .................. 260/293.3 P

OTHER PUBLICATIONS

Kump et al. "Helvetica Chimica Acta" vol. 56, (1973), pp. 2348–2377.

*Primary Examiner*—Henry R. Jiles
*Assistant Examiner*—Robert T. Bond
*Attorney, Agent, or Firm*—Oblon, Fisher, Spivak, McClelland & Maier

[57]   ABSTRACT

Rifamycin compounds having high antibiotic activity, comprising rose-colored powders, water insoluble, but soluble in most of the organic solvents.

Such compounds are obtained by reacting 3-amino-rifamycin S with gaseous ammonia in ethers and/or aromatic hydrocarbons at a temperature between 0° C and +30° C, stirring the mixture for at least 3 hours, and then isolating the compound thus obtained.

5 Claims, No Drawings

RIFAMYCIN COMPOUNDS

This invention relates to novel Rifamycin compounds having high antibiotic activity.

German Pat. No. 1,670,377 discloses 3-amino-rifamycin S having the following structural formula

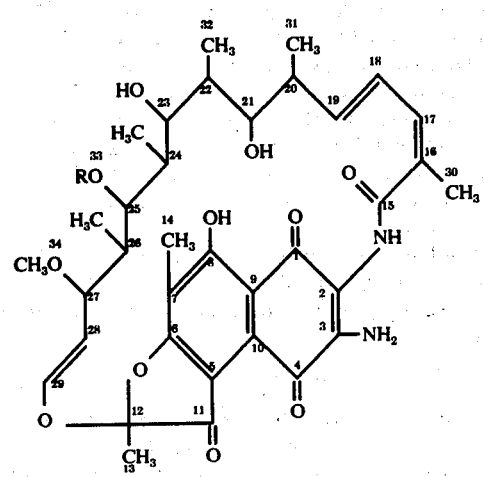
(II)

in which R is —COOH$_3$, and also its 16, 17, 18, 18 tetrahydroderivative and its 16, 17, 18, 19, 28, 29 hexahydroderivative are disclosed: such compounds exhibit antibiotic properties.

A method for obtaining the compound according to formula (II) has been carried into practice by the present Applicants and is described in German Patent Application DOS No. 2,548,148.

It is well known that respective 16, 17, 18, 19 tetrahydro-derivatives and 16, 17, 18, 19, 28, 29 hexahydroderivatives can be obtained from rifamycin compounds, the properties of which derivatives are comparable to those of the compounds from which they derive: the method for obtaining such derivatives is obvious to those skilled in the art and is described, for example, in the above mentioned German Pat. No. 1,670,377 and in Experientia 20, 336, (1964).

This invention relates to a rifamycin compound selected from the group consisting of a compound having the following structural formula:

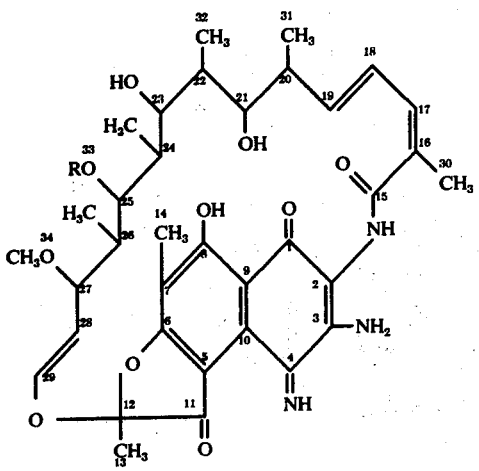
(I)

in which R is —H or —COOH$_3$, its 16, 17, 18, 19 tetrahydro-derivatives, and its 16, 17, 18, 19, 28, 29 hexahydroderivatives.

The present invention also relates to products provided by mild reduction of the compounds according to formula (I), having in turn the following structural formula (III):

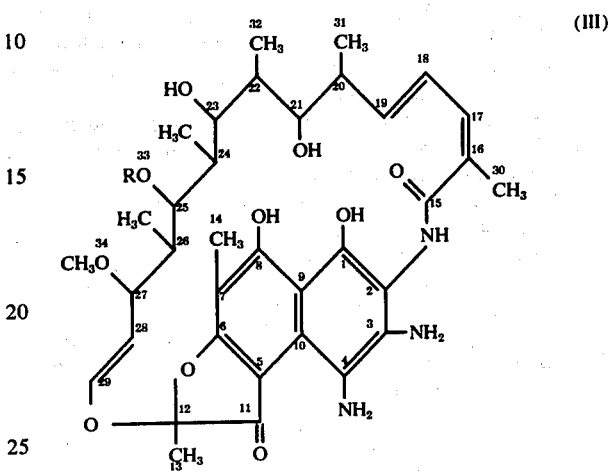
(III)

in which R is —H or —COOH$_3$, its 16, 17, 18, 19 tetrahydro-derivatives, 16, 17, 18, 19, 28, 29 hexahydroderivatives.

The rifamycin compounds according to the present invention have a powerful antibacterial activity on Gram-positive, Gram-Negative germs, and particularly on Mycobacterium Tuberculosis. Such compounds are rose-coloured powders, water insoluble, soluble in most of the organic solvents, such as chlorinated solvents, alcohols, esters, partially soluble in aromatic hydrocarbons, from which they can be crystallized.

In order that the characteristic features of the present invention be more clearly understood, some compounds and methods for obtaining the same will now be described by mere way of unrestrictive example.

EXAMPLE 1

20 g 3-amino-rifamycin S were dissolved at 20° C in 100 ml tetrahydrofuran saturated with gaseous ammonia. The solution was stirred at room temperature for 15 hours without further addition of ammonia. 200 ml dichloromethane were then added to the reaction solution, thoroughly washing with diluted acetic acid and then with water. The organic layer was dried on sodium sulphate and the solvent removed under reduced pressure.

The residue was recrystallized from 2-methoxyethanol.
Yield = 17 g.

The product thus obtained has the following characteristics:

— empirical formula: $C_{37}H_{47}N_3O_{11}$ in accordance with the results of the elemental analysis;
— I. R. spectrum in nujol oil of the product obtained from dichloromethane shows peak values at 3400 (shoulder), 3300, 1705, 1650, 1605, 1582, 1560 (shoulder), 1512, 1425, 1355, 1290, 1265, 1240, (shoulder), 1175, 1142, 1071, 1050, 1020 (shoulder), 970, 952, 920, 890, 840, 815 and 772 cm$^{-1}$;

— electronic absorption spectrum in methanol solution shows peak values at 475, 310, 270 and 235 nm;

— spectrum $^1$H NMR in $CDCl_3$ -$CD_3SOCD_3$ (1:1), using tetramethylsilane as the internal standard, shows the most significant peaks at $\delta$: -0.04($d$); +0.66($d$); +0.92($d$); +1.02($d$); +1.81 ($s$); +2.07($s$); +2.31($s$); +3.08($s$); +5.09($dd$); +5.25($d$); +5.8/6.7($m$); +8.70($s$); +14.13($s$) and +15.13($s$) ppm, the disappearance of the three peaks last mentioned when in presence of deuterated water being characteristic;

— spectrum $^{13}$C NMR in dioxane -$d_8$, using tetramethylsilane as the internal standard shows the most significant peaks at $\delta$ : 197.4; 184.7; 172.6; 172.4; 170.8 and 170.6 ppm, which, when compared with those of the similar spectra of the compounds according to formula (II), ratify that the product obtained has the formula (I), in which R is —$COCH_3$;

— thin layer chromatography on silica gel plate, eluent benzene-methylisobutylketone-methanol (5:5:1), gives Rf = 0.74.

EXAMPLE 2

28 g 3-amino-rifamycin S were dissolved in 200 ml dioxane and submitted to a slow but continuous ammonia stream for 10 hours at 15° C. The solution was stirred for further 10 hours at 15° C. The precipitate obtained was filtered, washed with a slight amount of cold dioxane, then with xylene, and finally with petroleum ether.

Yield = 20 g. The product obtained has the same chemical-physical properties as the product obtained according to Example 1.

EXAMPLE 3

21 g 3-amino-rifamycin S were dissolved in 150 ml dioxane at 23° C and saturated with gaseous ammonia. The solution was stirred for 15 hours at 23° C, saturating again with ammonia, and finally stirred for further 3 hours. 200 ml dichloromethane were added, washing with diluted acetic acid, and then with water. After drying on sodium sulphate, the solvent was evaporated under reduced pressure and the residue recrystallized from 2-methoxyethanol.

Yield = 16.8 g. Also in this case, the product obtained is identical to that of Example 1.

EXAMPLE 4

14 g product obtained as in Examples 1, 2 and 3 were mixed with 2 g zinc and stirred after addition of 60 ml acetic acid and 50 ml dioxane. After 15 minutes, excess zinc was filtered, then precipitating in 300 ml water containing 5 g EDTA and 30 g sodium chloride. The reaction product was refiltered, washed with water and dried. Yield = 11 g.

The product obtained is the reduced form of the initial or starting product. The electronic absorption spectrum in methanol solution shows peak values at 415 and 300 nm. Instead of using zinc in acetic acid as a reducing agent, iron in acetic acid can be used providing under the same reaction conditions the same final product.

EXAMPLE 5

10 g 3-amino-25-disacetyl-rifamicin S were dissolved in 150 ml tetrahydrofuran and the solution was kept under gaseous ammonia flow at 7° C for 4 hours. Then, operating as in Example 1, 9 g of a product were obtained that chromatographed on thin layer on silica gel plate gives by benzene-methylisobutylketone-methanol eluent system (5:5:1) Rf = 0.58. The compound obtained has the empirical formula $C_{35}H_{45}N_3O_{10}$.

EXAMPLE 6

14 g 3-amino-rifamycin S were dissolved in 70 ml ethylene glycol dimethyl ether at 27° C and exposed for 15 minutes to a slow but continuous gaseous ammonia flow. The solution was stirred for 3 hours. Then, the solution was saturated with gaseous ammonia, and allowed to react still at 27° C for further 16 hours. The reaction mixture was diluted with 200 ml dichloromethane, washed with diluted acetic acid and then again with water. The reaction product was dried on sodium sulphate, dichloromethane was evaporated and the residue recrystallized from benzene.

Yield = 12.5 g product identical to that obtained in Example 1.

EXAMPLE 7

7 g 3-amino-rifamycin S were mixted with 60 ml benzene at 18° C. Gaseous ammonia was bubbled for 10 minutes every second hour until tenth hour. The reaction mixture was diluted with 200 ml dichloromethane, washed with diluted acetic acid and then with water. The solution was dried on sodium sulphate and then evaporated to dryness.

By recrystallization from 2-methoxyethanol, 5.5 g were obtained of a product identical to that of Example 1.

By operating just as disclosed in the precedent examples, but using 3-amino-16, 17, 18, 19-tetrahydrorifamycin S and 3-amino-16, 17, 18, 19, 28, 29-hexahydrorifamycin S, respectively, as starting or initial compounds, corresponding 3-amino-4-desoxo-4-imino-16, 17, 18, 19-tetrahydrorifamycin S and corresponding 3-amino-4-desoxo-4-imino-16, 17, 18, 19, 28, 29-hexahydrorifamycin S, respectively, are obtained. The compounds thus obtained can be converted into the corresponding reduced products by operating in accordance with Example 4.

What we claim is:

1. A Rifamycin compound selected from the group consisting of a compound having the following formula:

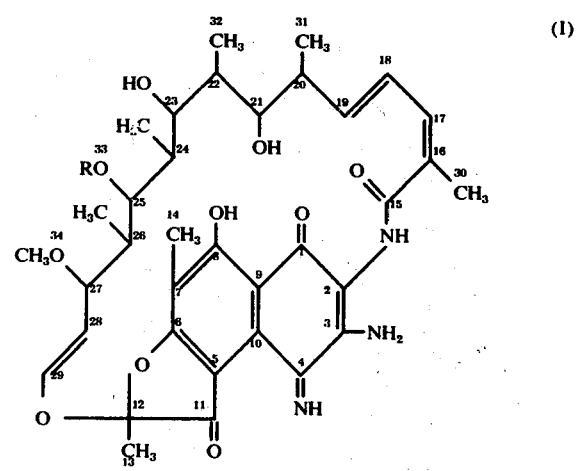

in which R is —H or —COCH₃, its 16, 17, 18, 19 tetrahydroderivatives, 16, 17, 18, 19, 28, 29 hexahydroderivatives and corresponding reduced products having the formula:

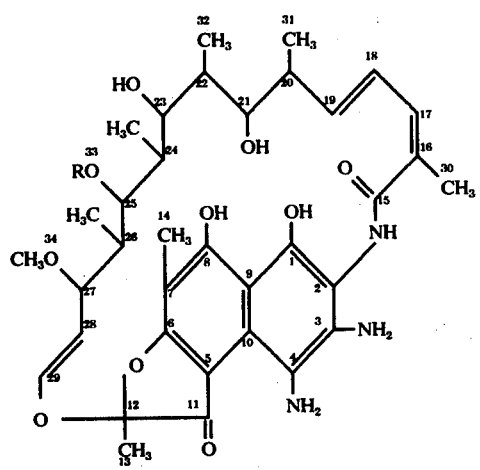

wherein R is —H or —COCH₃, its 16, 17, 18, 19 tetrahydroderivatives, 16, 17, 18, 19, 28, 29 hexahydroderivatives.

2. A method of preparing a Rifamycin compound of formula (I) of claim 1, comprising reacting a compound having the formula

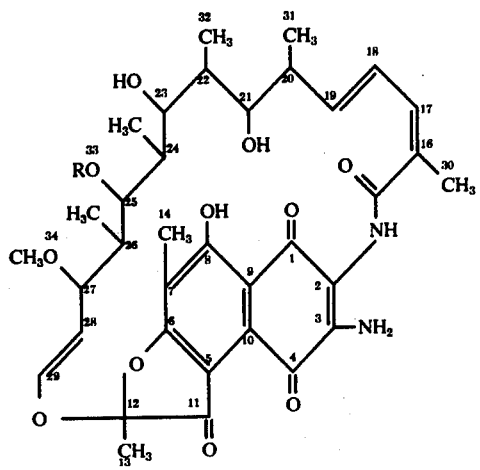

wherein R is —H or —COCH₃, in a solvent selected from the group consisting of ethers and aromatic hydrocarbons at a temperature of between 0° C and +30° C with gaseous ammonia, stirring said reaction mixture for at least 3 hours, and isolating the Rifamycin S compound of formula I of claim 1 thus obtained.

3. A method according to claim 2, wherein said solvent is selected from the group consisting of ethylene glycol dimethyl ether, tetrahydrofuran, dioxane and benzene.

4. A method according to claim 2, wherein the reaction temperature is of between +15° C and +25° C, and said reaction is continued for a time period of between 15 and 20 hours.

5. A method of preparing reduced products having the formula

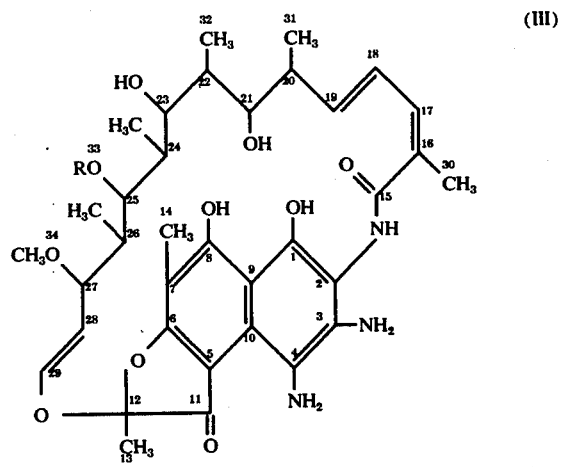

wherein R is —H or —COCH₃, the method comprising reacting the compound according to formula (I) with reducing agents selected from the group consisting of zinc in acetic acid and iron in acetic acid substantially at room temperature, and isolating from the reaction mixture the products thus obtained.

* * * * *

UNITED STATES PATENT AND TRADEMARK OFFICE
CERTIFICATE OF CORRECTION

PATENT NO. : 4,017,481
DATED : April 12, 1977
INVENTOR(S) : LEONARDO MARSILI ET AL It is certified that error appears in the above-identified patent and that said Letters Patent are hereby corrected as shown below:

Column 1, line 28 and Column 2, lines 1 and 28, delete "COOH$_3$" and insert therefor --COCH$_3$--.

Signed and Sealed this

Twenty-fifth Day of October 1977

[SEAL]

Attest:

RUTH C. MASON
*Attesting Officer*

LUTRELLE F. PARKER
*Acting Commissioner of Patents and Trademarks*